US007908010B2

(12) United States Patent
Greenberg et al.

(10) Patent No.: US 7,908,010 B2
(45) Date of Patent: *Mar. 15, 2011

(54) RETINAL PROSTHESIS WITH SIDE MOUNTED INDUCTIVE COIL

(75) Inventors: Robert Greenberg, Los Angeles, CA (US); Mark Humayan, Glendale, CA (US); James Little, Saugus, CA (US); Kevin Wilkin, Valencia, CA (US); Da-Yu Chang, Rowland Heights, CA (US); Rajat Agrawal, Pasadena, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 642 days.

This patent is subject to a terminal disclaimer.

(21) Appl. No.: 11/873,181

(22) Filed: Oct. 16, 2007

(65) Prior Publication Data

US 2008/0039936 A1    Feb. 14, 2008

Related U.S. Application Data

(62) Division of application No. 11/498,506, filed on Aug. 2, 2006, which is a division of application No. 10/820,240, filed on Apr. 6, 2004, now Pat. No. 7,228,181.

(51) Int. Cl.
*A61N 1/08*    (2006.01)
*A61N 1/18*    (2006.01)

(52) U.S. Cl. .......................................... 607/54

(58) Field of Classification Search .............. 607/53–54, 607/141, 139
See application file for complete search history.

(56) References Cited

U.S. PATENT DOCUMENTS

| | | | |
|---|---|---|---|
| 3,699,970 | A | 10/1972 | Brindley |
| 4,573,481 | A | 3/1986 | Bullara |
| 4,628,933 | A | 12/1986 | Michelson |
| 4,837,049 | A | 6/1989 | Byers |
| 5,109,844 | A | 5/1992 | de Juan |
| 5,215,088 | A | 6/1993 | Normann |
| 5,935,155 | A | 8/1999 | Humayun |
| 6,324,429 | B1 | 11/2001 | Shire |
| 6,358,281 | B1 * | 3/2002 | Berrang et al. ................. 623/10 |
| 6,400,989 | B1 | 6/2002 | Eckmiller |
| 6,458,157 | B1 | 10/2002 | Suaning |
| 6,718,209 | B2 | 4/2004 | Williamson |
| 6,847,847 | B2 | 1/2005 | Nisch et al. ..................... 607/54 |
| 7,228,181 | B2 * | 6/2007 | Greenberg et al. ............. 607/54 |
| 2002/0095193 | A1 | 7/2002 | Ok et al. |
| 2002/0198573 | A1 * | 12/2002 | Nisch et al. ..................... 607/54 |
| 2003/0097166 | A1 | 5/2003 | Krulevitch et al. ........... 607/116 |
| 2003/0139808 | A1 | 7/2003 | Shahinpoor et al. ........... 623/4.1 |
| 2003/0158588 | A1 | 8/2003 | Rizzo et al. ..................... 607/54 |
| 2004/0117011 | A1 * | 6/2004 | Aharoni et al. .............. 623/6.11 |
| 2004/0127957 | A1 * | 7/2004 | Fujikado et al. ................ 607/54 |

* cited by examiner

*Primary Examiner* — Carl H Layno
*Assistant Examiner* — Jessica Sarcione
(74) *Attorney, Agent, or Firm* — Scott B. Dunbar; Tomas Lendvai

(57) ABSTRACT

The invention is a retinal prosthesis with an inductive coil mounted to the side of the eye by means of a strap around the eye. This allows for close coupling to an external coil and movement of the entire implanted portion with movement of the eye ball.

18 Claims, 6 Drawing Sheets

RETINAL PROSTHESIS WITH SIDE MOUNTED INDUCTIVE COIL

CROSS-REFERENCE TO RELATED APPLICATIONS

This patent application is a continuation application of U.S. patent application Ser. No. 11/498,506 filed on Aug. 2, 2006 which, in turn, is a divisional application of U.S. patent application Ser. No. 10/820,240, filed Apr. 6, 2004, for Retinal Prosthesis with Side Mounted Inductive Coil, now U.S. Pat. No. 7,228,181, the disclosure of which is incorporated herein by reference.

GOVERNMENT RIGHTS NOTICE

This invention was made with government support under grant No. R24EY12893-01. The government has certain rights in the invention.

FIELD OF THE INVENTION

The present invention is generally directed to a visual prosthesis and more specifically to an improved mechanical and electrical configuration for retinal prosthesis for artificial vision.

BACKGROUND OF THE INVENTION

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Humayun, U.S. Pat. No. 5,935,155 describes the use of retinal tacks to attach a retinal array to the retina. Alternatively, an electrode array may be attached by magnets or glue. U.S. Pat. No. 5,109,844 to de Juan describes a flat electrode array placed against the retina for visual stimulation.

Any device for stimulating percepts in the retina must receive a signal describing a visual image along with power to operate the device. The device can not be powered by wires as any connection through the skin will create the risk of infection. Battery power is not practical as batteries are bulky and surgery is required to replace them. Such signal and power may be transmitted into the eye inductively as shown in Humayun U.S. Pat. No. 5,935,155. Humayun uses a primary (external) coil in front of the eye, possibly encased within the rim of a pair of glasses, and a secondary (internal) coil within the lens capsule or around the sclera just under the conjunctiva. Implanting within the lens capsule is difficult surgery and only allows for a small diameter coil. Larger coils are more efficient, can receive more power with less resulting temperature rise per unit of power received. Implanting around the sclera under the conjunctiva and near the surgical limbus (that is at the front of the eye) allows for a larger coil but may cause irritation or damage to the conjunctiva if the coil is placed in front near the cornea.

U.S. patent application Ser. No. 09/761,270, Ok, discloses several coil configurations including a configuration where the coil is offset about 45 degrees from the front of the eye. The offset configuration allows the primary and secondary coils to be placed closer together allowing for better inductive coupling. The bridge of nose partially blocks placement of a primary coil when placed directly in front of the eye.

A better configuration is needed allowing for close physical spacing of relatively large primary and secondary coils, without causing physical damages such as erosion of the conjunctiva.

SUMMARY OF THE INVENTION

The invention is a retinal prosthesis with an inductive coil mounted to the side of the eye by means of a strap around the eye. This allows for close coupling to an external coil and movement of the entire implanted portion with movement of the eye ball.

Applicants have discovered that a coil around the sclera at or near 90 degrees rotation toward the lateral side of the eye has several advantages over previous designs. The secondary coil will not irritate the conjunctiva as it is placed against the sclera under the lateral rectus muscle, well behind the region where the conjunctiva attaches to the surgical limbus which is most susceptible to irritation. There is also more room between the conjunctiva and sclera on the side of the eye compared to the front of the eye. The primary coil can be placed on the temples of a pair of glasses and/or hidden by the user's hair. The spacing between primary and secondary coil can be as close, or closer, than that allowed for a coil pair located in the front of the eye or at a 45 degree angle because there are no eyelids or eyelashes to interfere with the coil.

The skull is relatively flat and thin at the temple outside the lateral side of the eye. This allows for close coupling of the primary and secondary coils. The secondary coil can be mounted on the sclera under the lateral rectus muscle allowing the coil to move with the eye, avoiding the need for a cable that flexes with eye movement.

A coil on the lateral side of the eye may be attached with a strap similar to a scleral buckle. A scleral buckle is a band of silicone placed around the eye and attached with a Watzke sleeve. A Watzke sleeve is a friction device that connects two silicone bands and holds them together with friction. Scleral buckles have been used to help hold the sclera against the retina when the retina has become detached. Scleral buckles are well known and many surgeons are skilled in their use, but using them to secure a device outside the eye is novel. Hence the secondary coil can be attached to, or integrated with, the strap and the strap placed around the sclera. In addition, suture tabs may be placed on the secondary coil to suture the coil to the sclera. The coil could also be affixed just by suturing to the sclera, without the use of a buckle.

In another alternative, the device may initially float and become secured by the growth of the natural foreign body reaction to the presence of the device in the body.

Further, an implanted electronics package is required to process and send the visual signal to the electrodes. It is advantageous to place the electronics package outside the sclera to aid heat dissipation. The electronics package can be attached to the strap or directly to the coil. This would not be possible with a front coil configuration as there is not enough room under the conjunctiva to accommodate the electronics package and coil near the limbus.

Blind people are conscious of their appearance. Hence, the reason for hiding the primary coil in a pair of glasses. A coil on the side of the head can be hidden under the user's hair and/or incorporated in the design of glasses.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
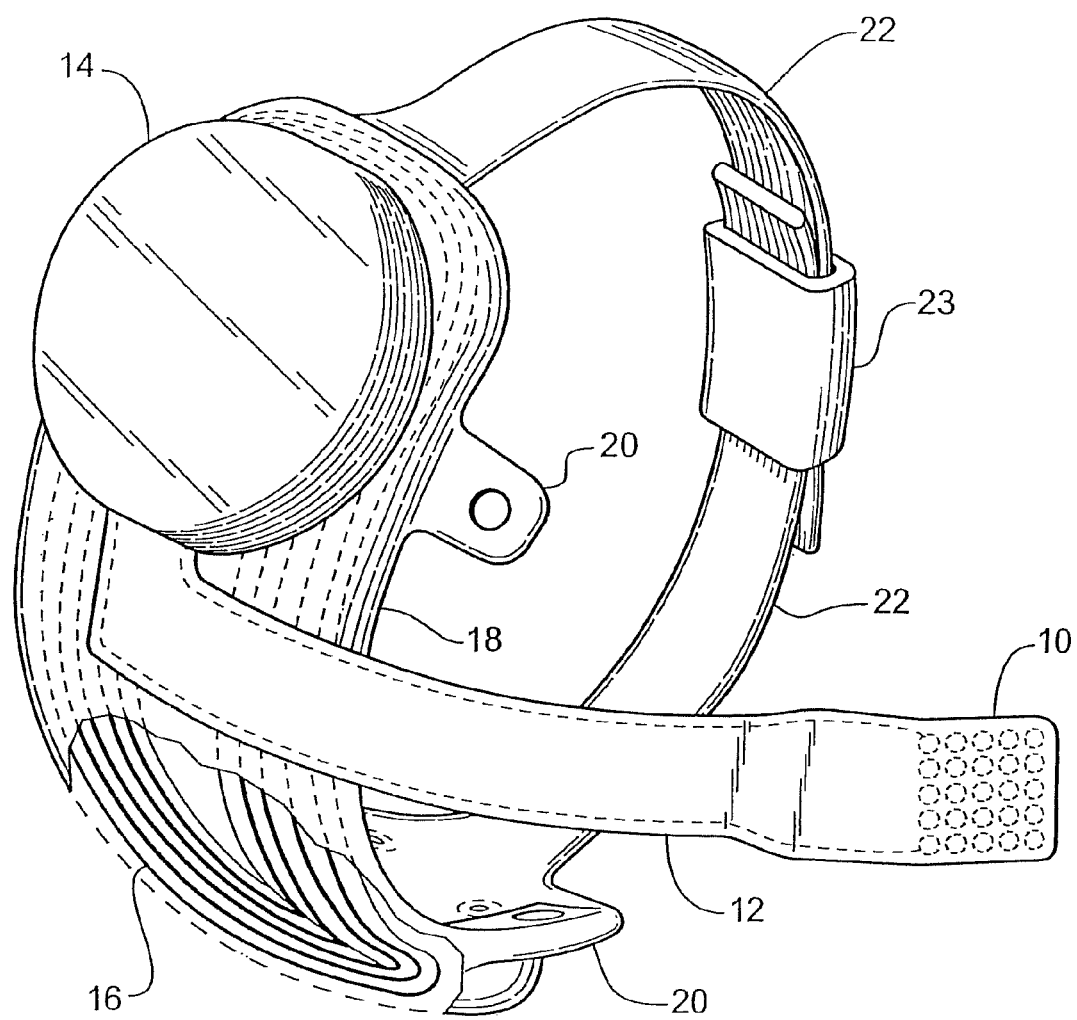
FIG. 1 is a perspective view of the implanted portion of the preferred retinal prosthesis.

FIG. 1 shows a perspective view of the implanted portion of the preferred retinal prosthesis. An electrode array 10 is mounted by a retinal tack or similar means to the epiretinal surface. The electrode array 10 is electrically coupled by a cable 12 which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil may be made from a thin film polymer sandwich with wire traces deposited between layers of thin film polymer. The electronics package 14 and secondary inductive coil 16 are held together by a molded body 18. The molded body 18 may also include suture tabs 20. The molded body narrows to form a strap 22 which surrounds the sclera and holds the molded body 18, secondary inductive coil 16, and electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap can better support an oval shaped coil.

It should be noted that the entire implant is attached to and supported by the sclera. An eye moves constantly. The eye moves to scan a scene and also has a jitter motion to improve acuity. Even though such motion is useless in the blind, it often continues long after a person has lost their sight. It is an advantage of the present design, that the entire implanted portion of the prosthesis is attached to and supported by the sclera. By placing the device under the rectus muscles with the electronics package in an area of fatty issue between the rectus muscles, eye motion does not cause any flexing which might fatigue, and eventually damage, the device.

Figure 2:
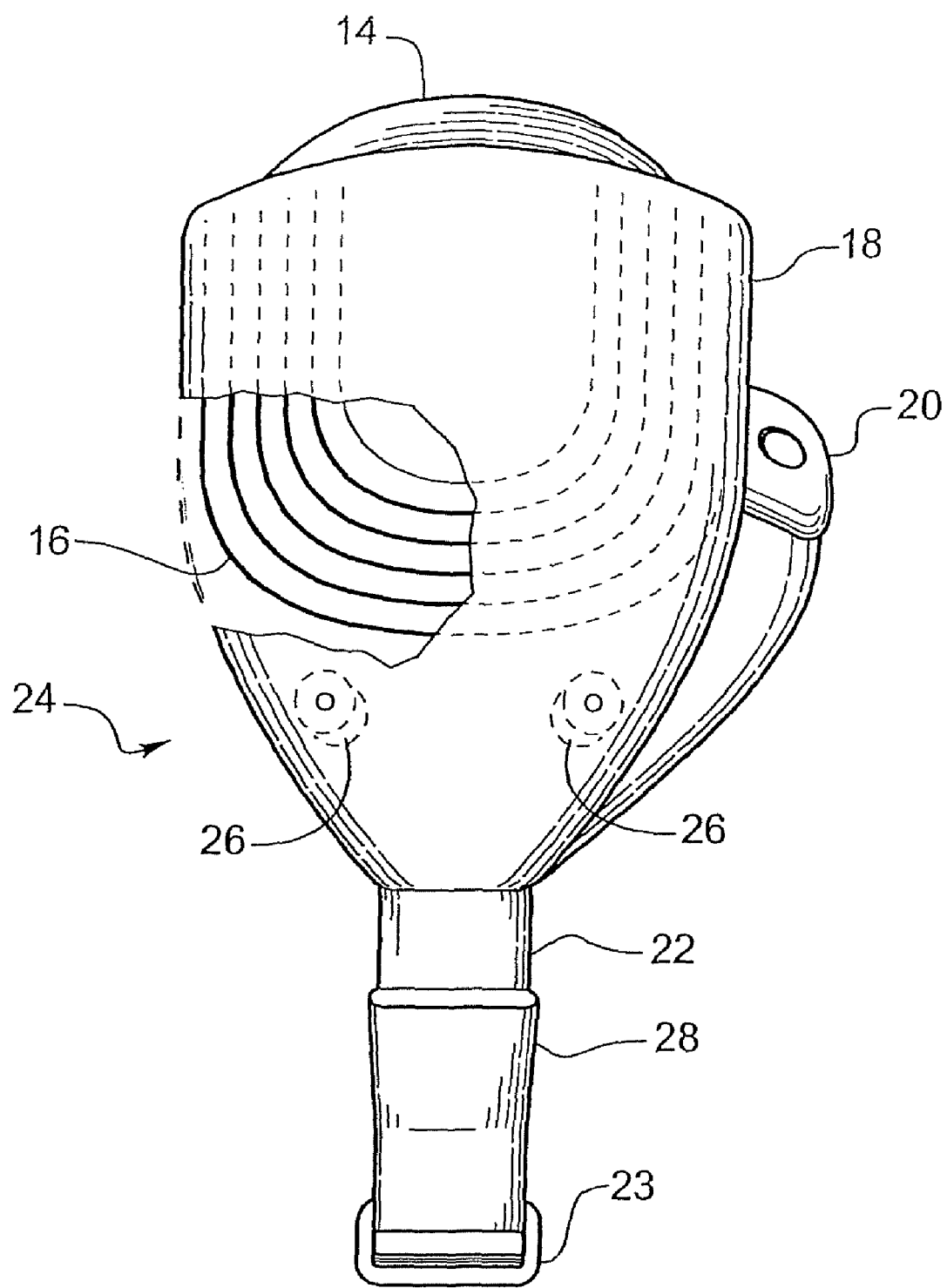
FIG. 2 is a side view of the implanted portion of the preferred retinal prosthesis showing the fan tail in more detail.

FIG. 2 shows a side view of the implanted portion of the retinal prosthesis, in particular, emphasizing the fan tail 24. When implanting the retinal prosthesis, it is necessary to pass the strap 22 under the eye muscles to surround the sclera. The secondary inductive coil 16 and molded body 18 must also follow the strap under the lateral rectus muscle on the side of the sclera. The implanted portion of the retinal prosthesis is very delicate. It is easy to tear the molded body 18 or break wires in the secondary inductive coil 16. In order to allow the molded body 18 to slide smoothly under the lateral rectus muscle, the molded body is shaped in the form of a fan tail 24 on the end opposite the electronics package 14.

Figure 3:
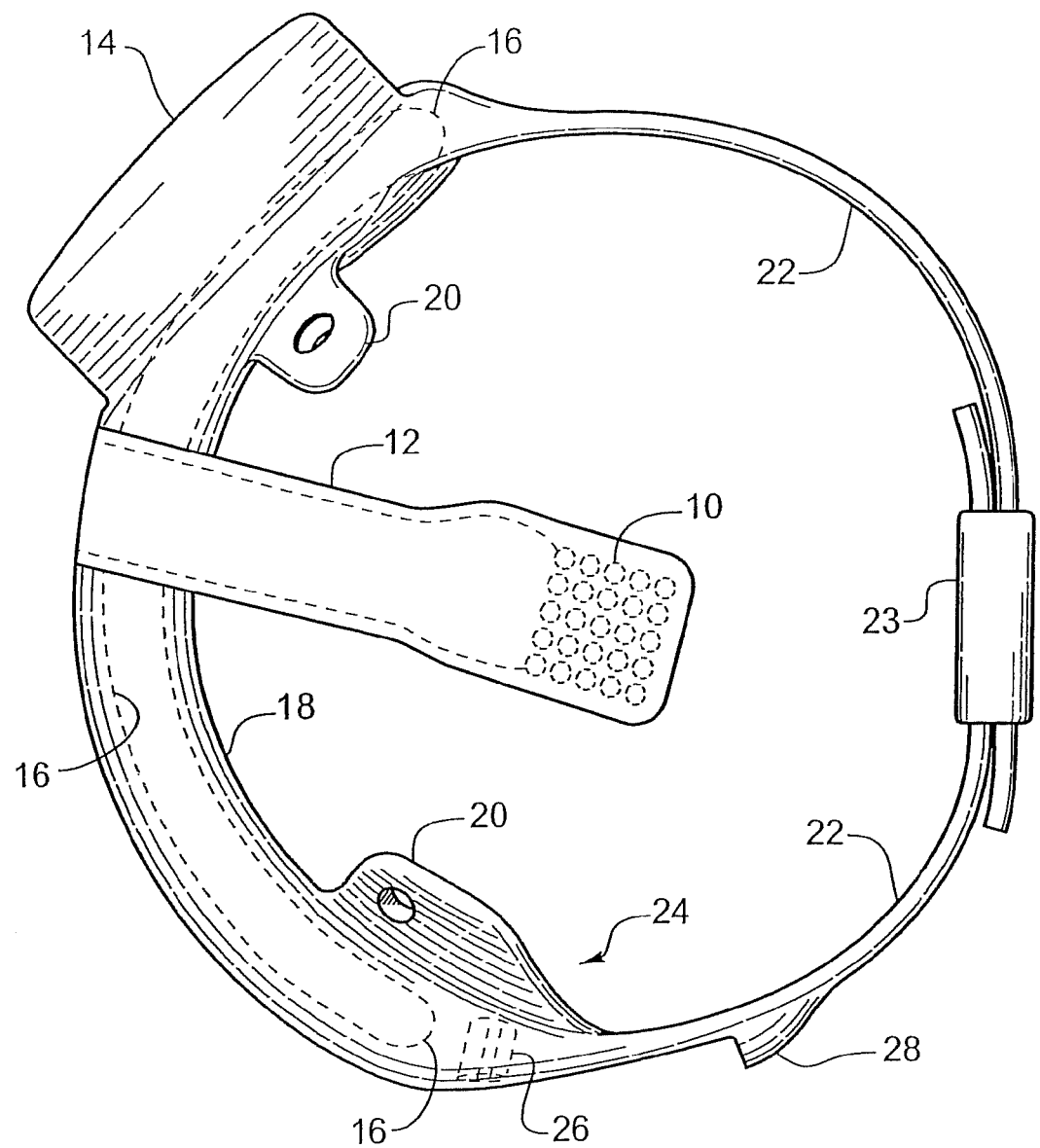
FIG. 3 is an edge view of the implanted portion of the preferred retinal prosthesis showing the hook for aiding the implantation of the retinal prosthesis.

Reinforced attachment points 26 are provided to facilitate handling of the retinal prosthesis by surgical tools. Preferably, the reinforced attachment points are harder silicone formed around holes through the molded body 18. Further, a hook 28 is molded into the strap 22 just beyond the end of the fan tail 24. A surgical tool can be used against the hook 28 to push the strap 22 under the rectus muscles. The hook 28 is more clearly depicted by the edge view of FIG. 3. The strap 22 is attached to itself by a sleeve 23. The sleeve 23 is a friction device that connects two silicone bands and holds them together with friction. The sleeve 23 is similar to a Watzke sleeve, used with a scleral buckle, and is well known in the art.

In the preferred embodiment, the electrode array 10 and cable 12 are formed layers of a thin polymer film with metal traces sandwiched between the thin polymer films. In such an embodiment, it is advantageous that the film with openings for electrode array 10 be the same film with an opening for connection to the electronics package 14. Therefore, the cable 12 exits the electronics package up away from the fantail 24, folds over itself and exits down toward the fantail 24, before turning at a right angle and piercing the sclera. This allows the same side of the cable to face both the electronics package and the retina. The cable 12 may also include a fantail at the point it is attached to the electronics package 14 and at the point it is attached to the electrode array 10 to reduce any stress on the connections that may be caused by implantation. It is important that the cable exit the molded body 18 toward the front of the eye. The cable must travel above the lateral rectus muscle and pierce the sclera at the pars plana, in front of the retina, so it does not damage the retina. Once inside the eye, the cable 12 can fold back over the retina to properly locate the electrode array 10 on the epiretinal surface.

Figure 4:
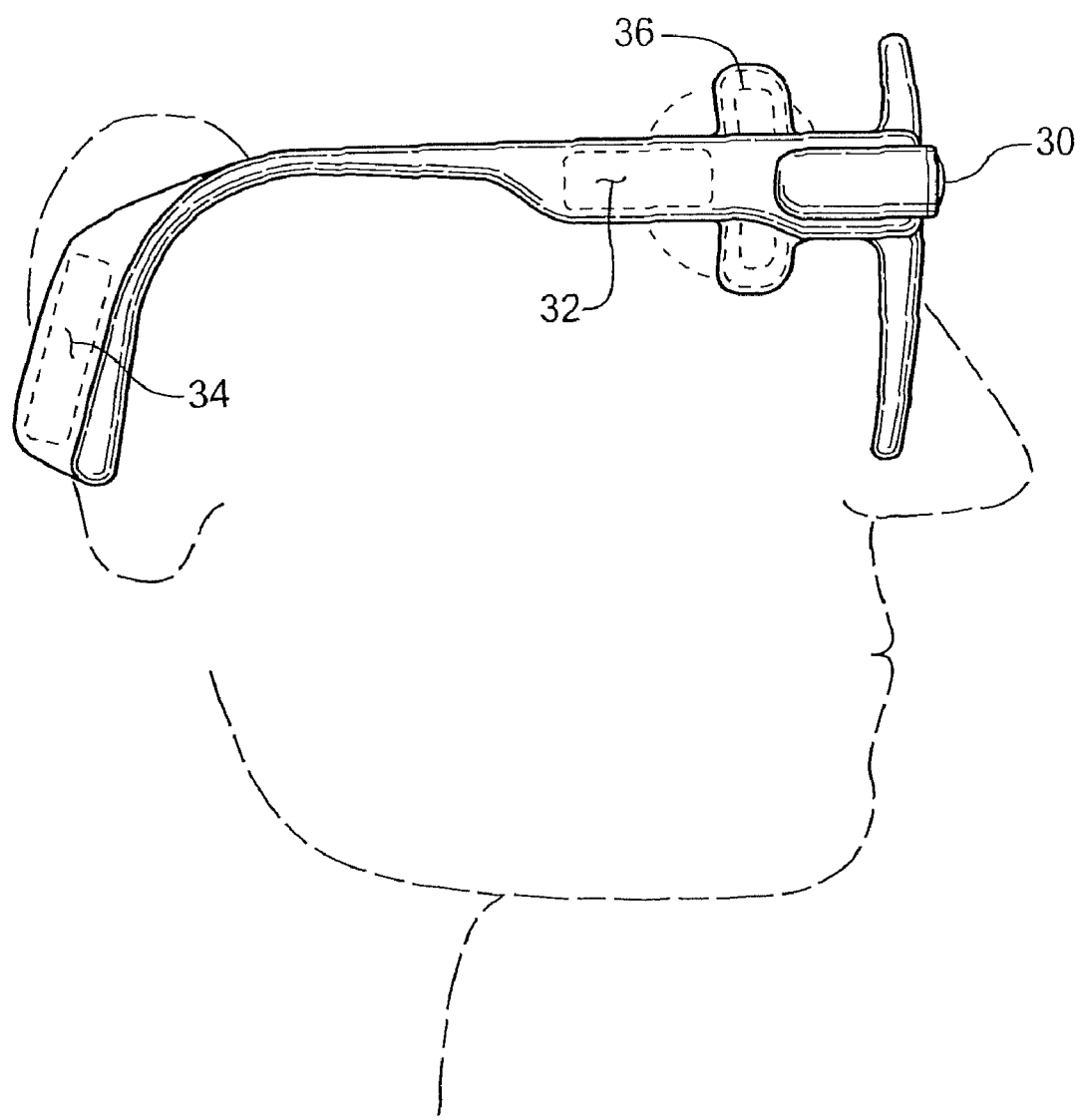
FIG. 4 is an external profile view of a user wearing the external portion of the retinal prosthesis.

FIG. 4 depicts the profile of a user wearing the external portion of the retinal prosthesis. The entire device may be built into the temple of a pair of glasses. A camera 30 collects a video image and transmits data to an external electronics package 32. A battery 34 powers the camera 30, external electronics package 32, and provides power to a primary inductive coil 36. The primary inductive coil 36 sends power and data through the skin and skull to the secondary inductive coil 16. Maximum efficiency is obtained when the primary inductive coil 36 and secondary inductive coil 16 are the same size, shape and as close together as possible.

Figure 5:
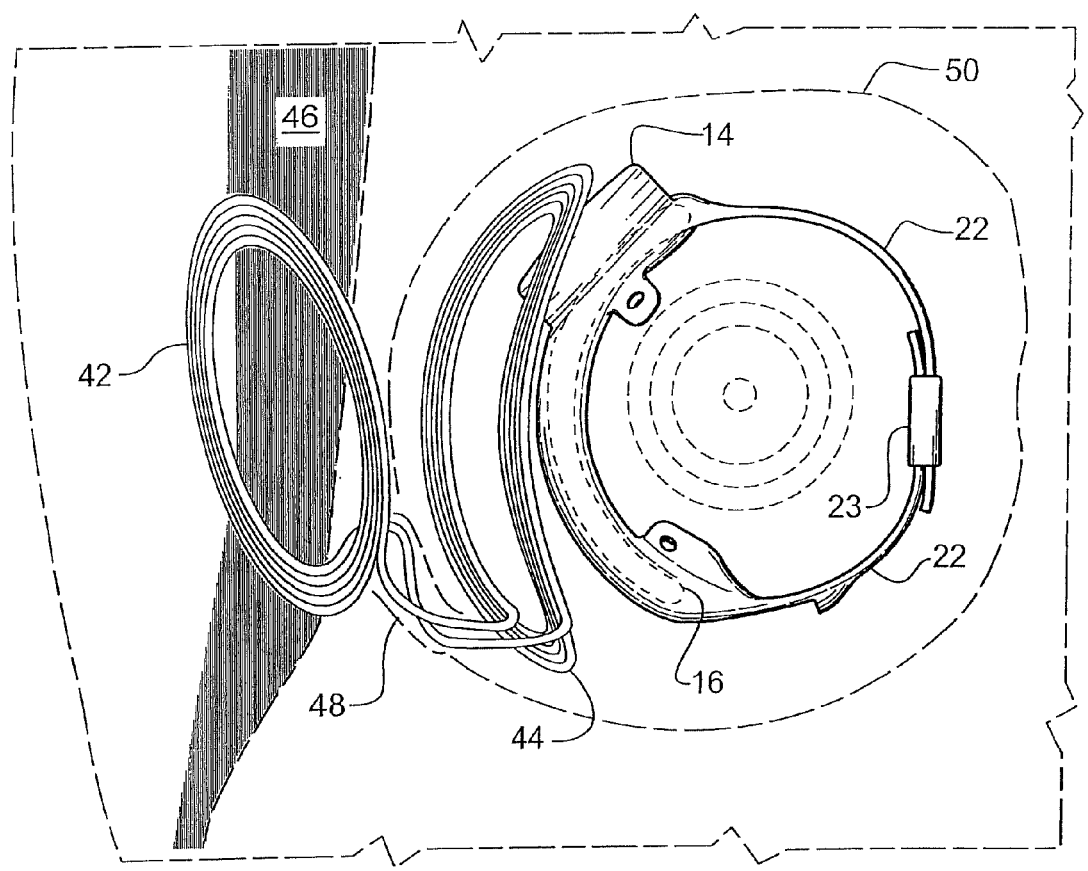
FIG. 5 shows an alternate embodiment using a passive repeater coil pair.

Referring to FIG. 5, an alternate embodiment uses a passive repeater coil pair. A passive secondary coil 42 is placed on the side of the scull in the temple region. Preferably, the passive secondary coil 42 is mounted just under the skin and attached to the temporalis muscle. Alternatively, the passive secondary coil 42 can be mounted wing of spheroid 46 (bone) just under the temporalis muscle. Once attached, wires may be routed though the inferior orbital fissure 48 into the eye socket 50, where a passive primary coil 44 is mounted to the scull inside the eye socket just over the lateral rectus muscle.

The passive secondary coil 42 and passive primary coil 44 form the passive repeater coil pair. The passive repeater coil pair simply makes a more efficient path for power and data to travel from the primary inductive coil 36 to the secondary inductive coil 16.

Figure 6:
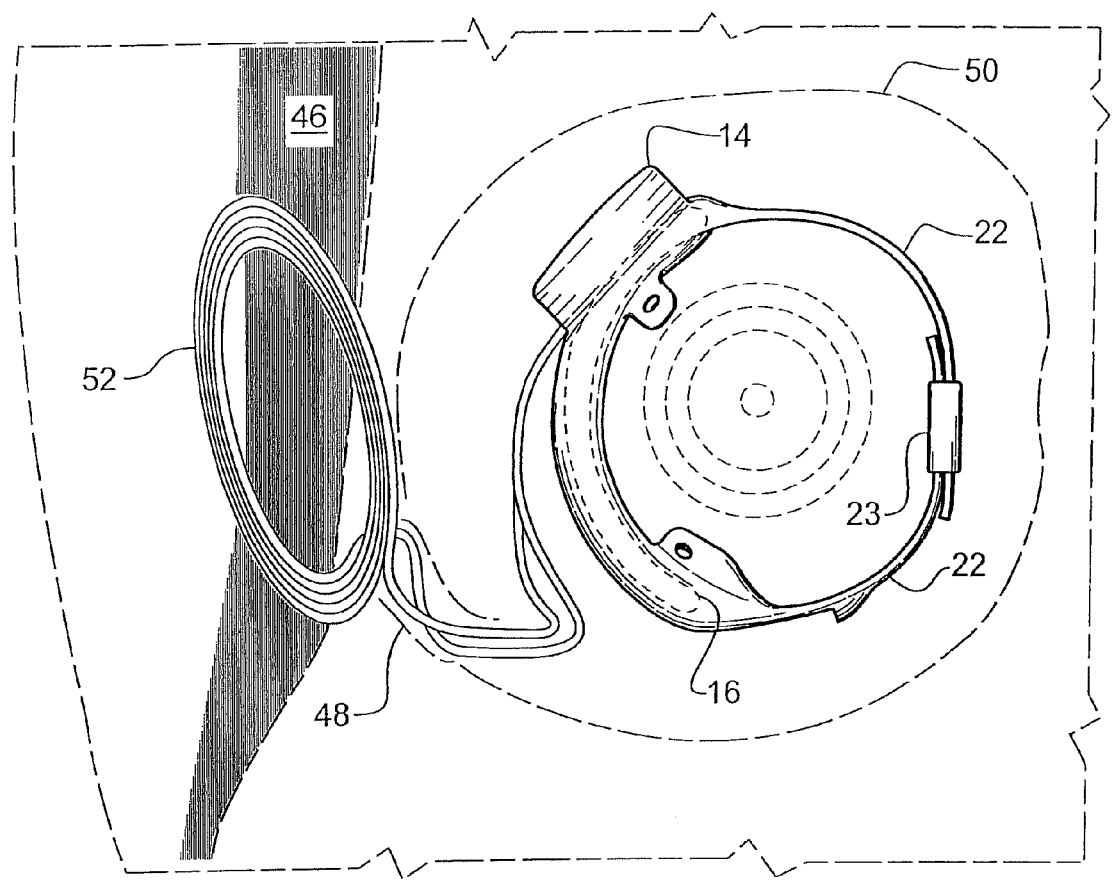
FIG. 6 show a second alternate embodiment using a coil in the temple region of the scull.

Referring to FIG. 6, a second alternate embodiment provides a remote secondary to inductive coil 52, mounted the same as the passive secondary coil 42. In this second alternative embodiment, wires from the remote secondary inductive coil 52 go directly to the electronics package 14. The electronics package 14 may be mounted with the remote secondary inductive coil 52 or on the sclera like the preferred embodiment. In either case, this second alternative embodiment provides the most efficient power use due to the close spacing of the primary inductive coil 36 and remote secondary inductive coil 52. However, this embodiment requires wires sufficiently flexible to accommodate eye movement without work hardening to the point a breaking.

Accordingly, what has been shown is an improved retinal prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The invention claimed is:

1. A visual prosthesis comprising:
   an electrode array suitable to be mounted in close proximity to visual neurons;
   an implanted electronics package;
   an electrical cable coupling said electrode array to said implanted electronics package;
   a secondary inductive coil, electrically coupled to said implanted electronics package;
   a frame suitable to be supported by a user's ears and nose;
   a primary inductive coil supported by said frame and inductively coupled with said secondary inductive coil;
   a battery supplying power to said primary inductive coil and supported by said frame;
   wherein said primary inductive coil and said battery are separately located on said frame; and an external electronics unit supported by said frame, powered by said battery and supplying a signal to said primary inductive coil.

2. The visual prosthesis according to claim 1, further comprising a strap connected to said secondary inductive coil and suitable to surround a sclera.

3. The visual prosthesis according to claim 2, further comprising a fan tail, having a decreasing radius of curvature, connected to said secondary inductive coil and to said strap.

4. The visual prosthesis according to claim 2, further comprising a hook on said prosthesis suitable for engaging a surgical tool.

5. The visual prosthesis according to claim 2, further comprising a sleeve for attaching ends of said strap together.

6. The visual prosthesis according to claim 1, wherein said cable and electrode array comprise metal traces sandwiched between thin polymer films.

7. The visual prosthesis according to claim 1, further comprising a strap connected to said implanted electronics package and suitable to surround a sclera.

8. The visual prosthesis according to 1, further comprising:
a first passive coil suitable be mounted within the body on the side of a skull; and
a second passive coil electrically coupled to said first passive coil and suitable to be mounted within the body proximate to said secondary inductive coil.

9. The visual prosthesis according to claim 1, further comprising suture tabs connected to said implanted electronics package suitable for attaching said electronics package to a sclera.

10. The visual prosthesis according to claim 1, further comprising a camera supported by said frame and supplying video data to said external electronics unit.

11. The visual prosthesis according to claim 10, wherein said camera is supported by said frame and is suitable to be placed on a side of a user's head.

12. The visual prosthesis according to claim 1, wherein said battery is supported by said frame and is suitable to be placed on a side of the user's head.

13. The visual prosthesis according to claim 1, wherein said battery is supported by said frame and is suitable to be placed behind the user's ear.

14. The visual prosthesis according to claim 1, wherein said external electronics unit is interposed between said primary inductive coil and said battery on a side of said frame.

15. The visual prosthesis according to claim 1, wherein the primary inductive coil is spaced apart from said battery.

16. The visual prosthesis according to claim 1, wherein the primary inductive coil is located on a front region of said frame and said said battery is located on a rear region of the frame.

17. The visual prosthesis according to claim 1, wherein the primary inductive coil is located on a front region of said frame and said battery is suitable to be located behind the user's ear.

18. A visual prosthesis comprising:
an electrode array suitable to be mounted in close proximity to visual neurons;
an implanted electronics package;
an electrical cable coupling said electrode array to said implanted electronics package;
a secondary inductive coil, electrically coupled to said implanted electronics package;
a frame suitable to be supported by a user's ears and nose;
a primary inductive coil supported by said frame and inductively coupled with said secondary inductive coil;
a camera supported by said frame supplying video data to said primary inductive coil;
a battery supplying power to said primary inductive coil and said camera, and supported by said frame; and an external electronics unit supported by said frame, powered by said battery, and receiving video data from said camera and supplying video data to said primary inductive coil.

* * * * *